United States Patent [19]

Corcoran

[11] Patent Number: 5,736,939

[45] Date of Patent: Apr. 7, 1998

[54] APPARATUS AND METHOD FOR DETERMING A CONDITION OF A ROAD

[75] Inventor: Paul T. Corcoran, Washington, Ill.

[73] Assignee: Caterpillar Inc., Peoria, Ill.

[21] Appl. No.: 763,649

[22] Filed: Dec. 11, 1996

[51] Int. Cl.[6] .................................................. G08G 1/09
[52] U.S. Cl. ...................... 340/905; 340/442; 364/424.07
[58] Field of Search ............................. 340/905, 901, 340/425.5, 447, 438; 364/424.07, 423.098; 180/167, 271

[56] References Cited

U.S. PATENT DOCUMENTS

| 4,003,241 | 1/1977 | Thomas. | |
|---|---|---|---|
| 4,635,739 | 1/1987 | Foley et al. | 177/45 |
| 4,839,835 | 6/1989 | Hagenbuch | 364/567 |
| 4,866,419 | 9/1989 | Kyrtsos et al. | 340/443 |
| 5,056,354 | 10/1991 | Kuwaha et al. | 73/146 |
| 5,182,712 | 1/1993 | Kyrtsos et al. | 364/424.07 |
| 5,497,100 | 3/1996 | Reiser et al. | 324/643 |
| 5,521,580 | 5/1996 | Kaneko et al. | 340/438 |
| 5,521,594 | 5/1996 | Fukushima | 340/904 |
| 5,531,122 | 7/1996 | Chatham et al. | 73/760 |
| 5,619,193 | 4/1997 | Doherety et al. | 340/905 |
| 5,647,439 | 7/1997 | Burdick et al. | 364/424.07 |

OTHER PUBLICATIONS

Application S/N 8/616,869, "Method For Detecting an Abnormal Condition of a Road Surface" filed Mar. 15 1996, Docket No. 94–246.

Application S/N 8/617,525, "Method for Determining The Resistance Factor of an Earthmoving Machine to Detect an Abnormal Condition" –Mar.15 1996.

Primary Examiner—Brent A. Swarthout

[57] ABSTRACT

An apparatus and method to determine a condition of a road traversed by at least one load hauling machine including at least one parameter sensor adapted to sense a parameter of the load hauling machine and responsively deliver a parameter signal, and a control system adapted to monitor a condition of a plurality of tires and responsively generate a calibration signal.

21 Claims, 6 Drawing Sheets

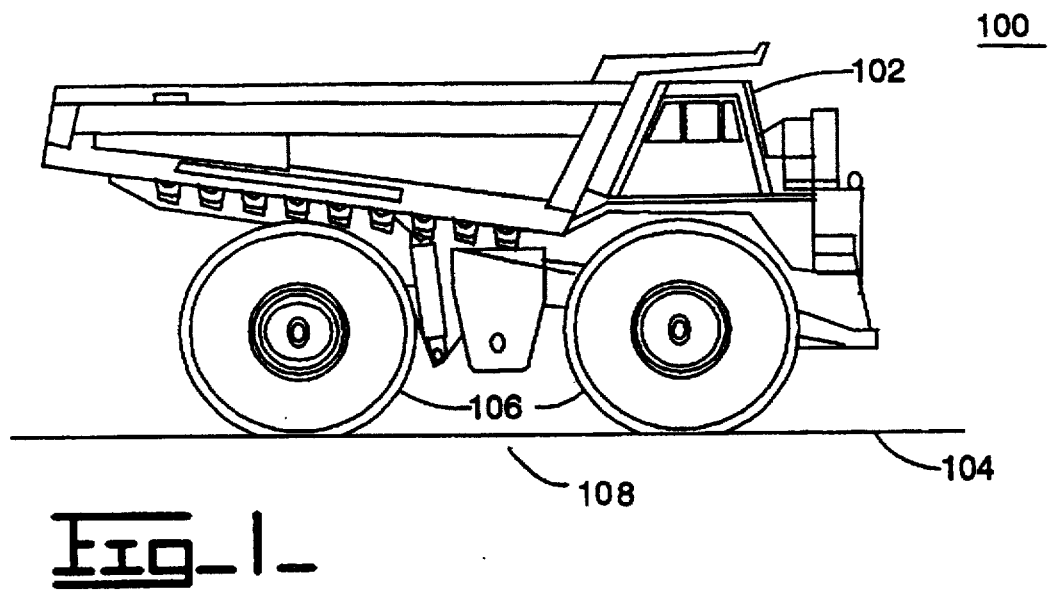
Fig_1_
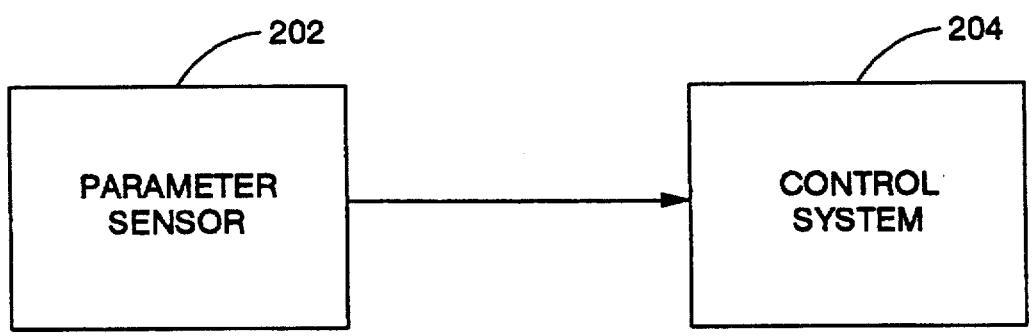
Fig_2_

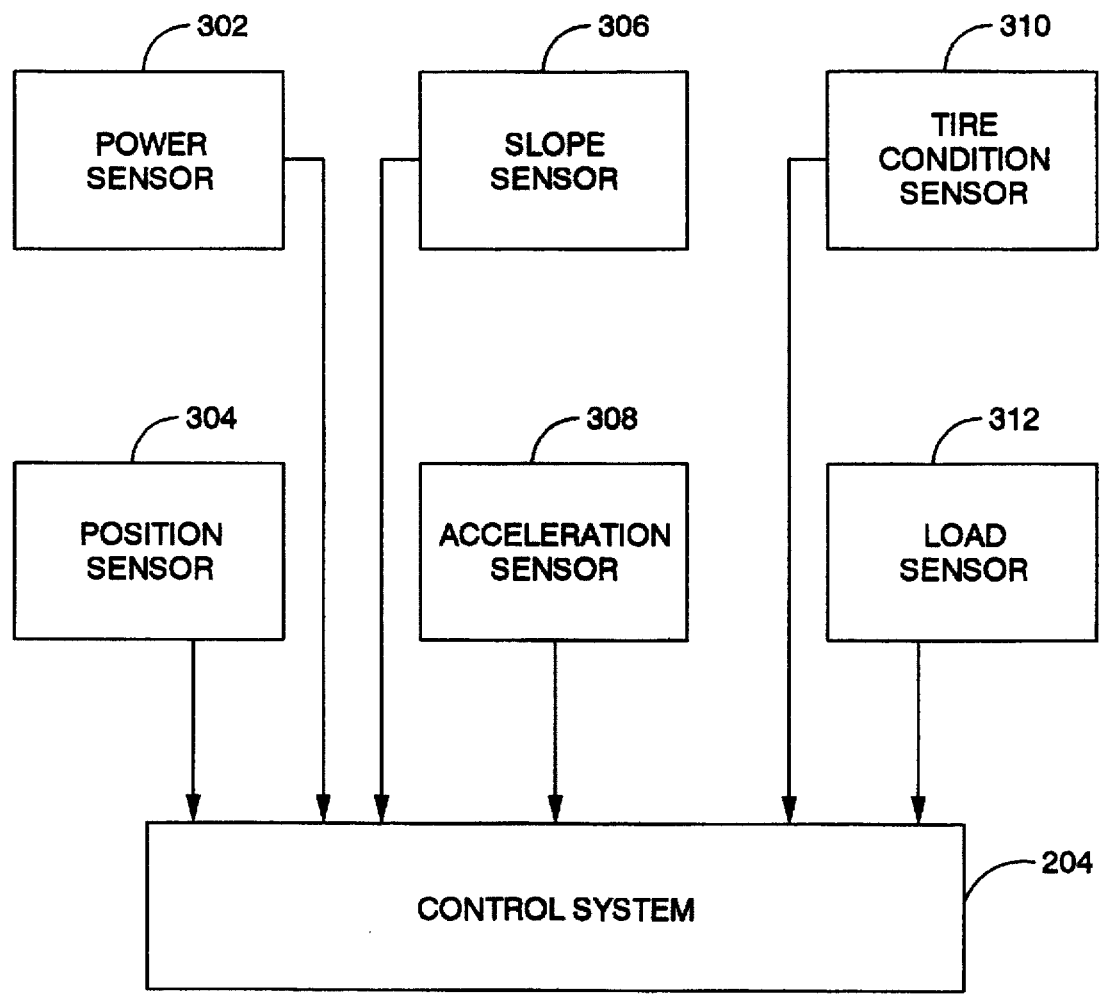
Fig_3_

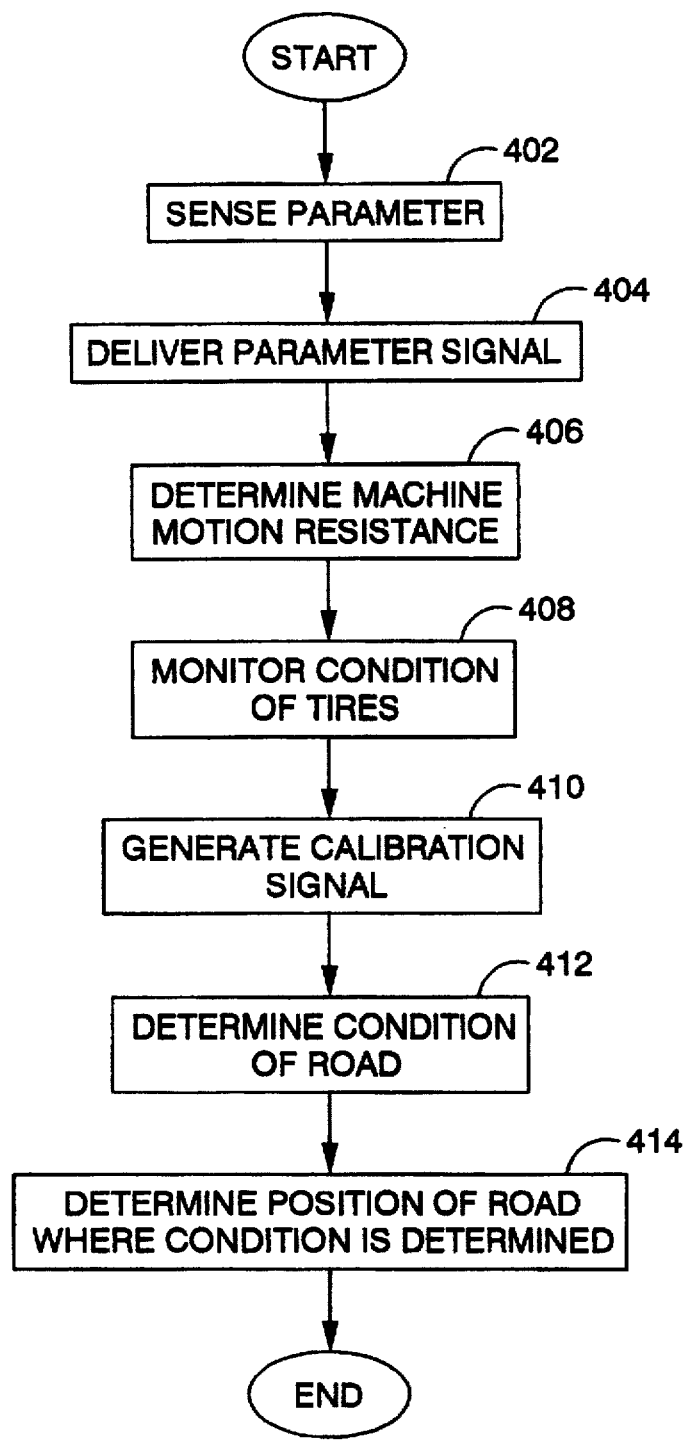
Fig_4_

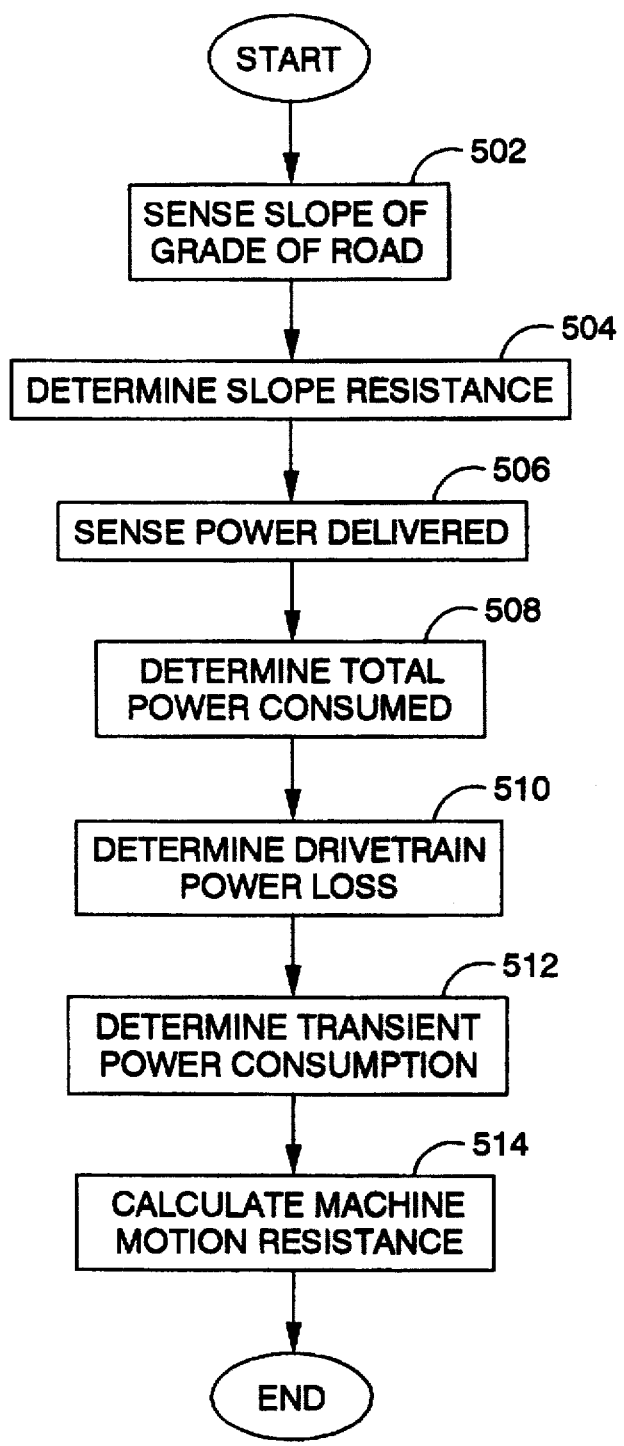
Fig_5_

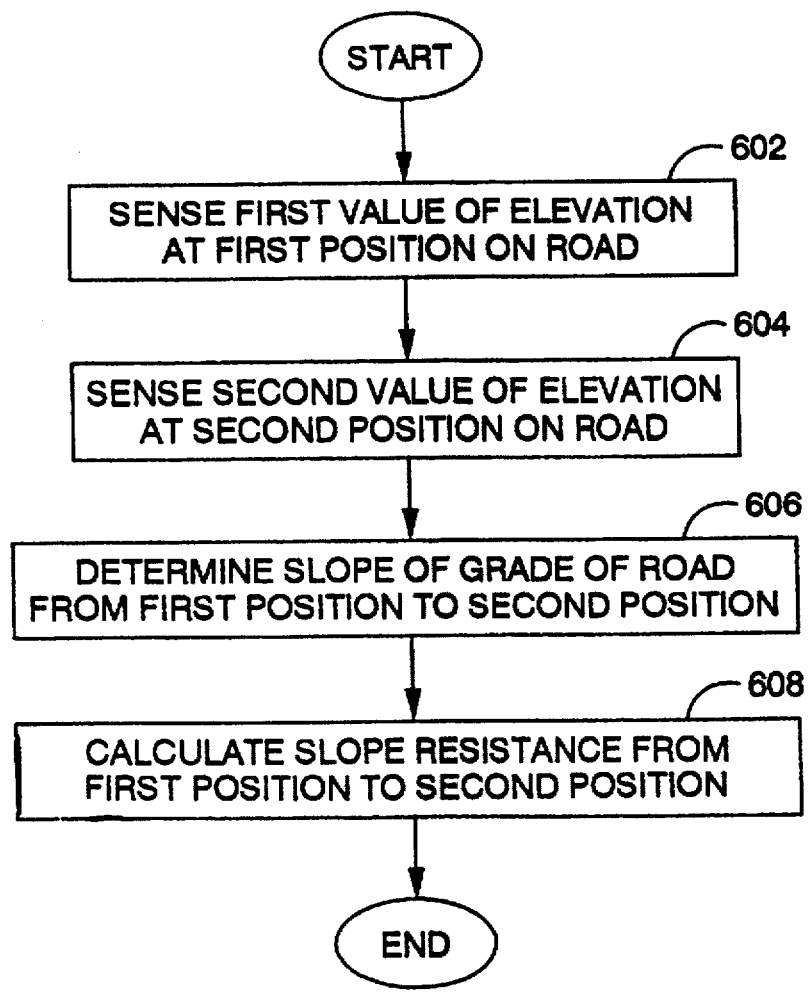
Fig_6_

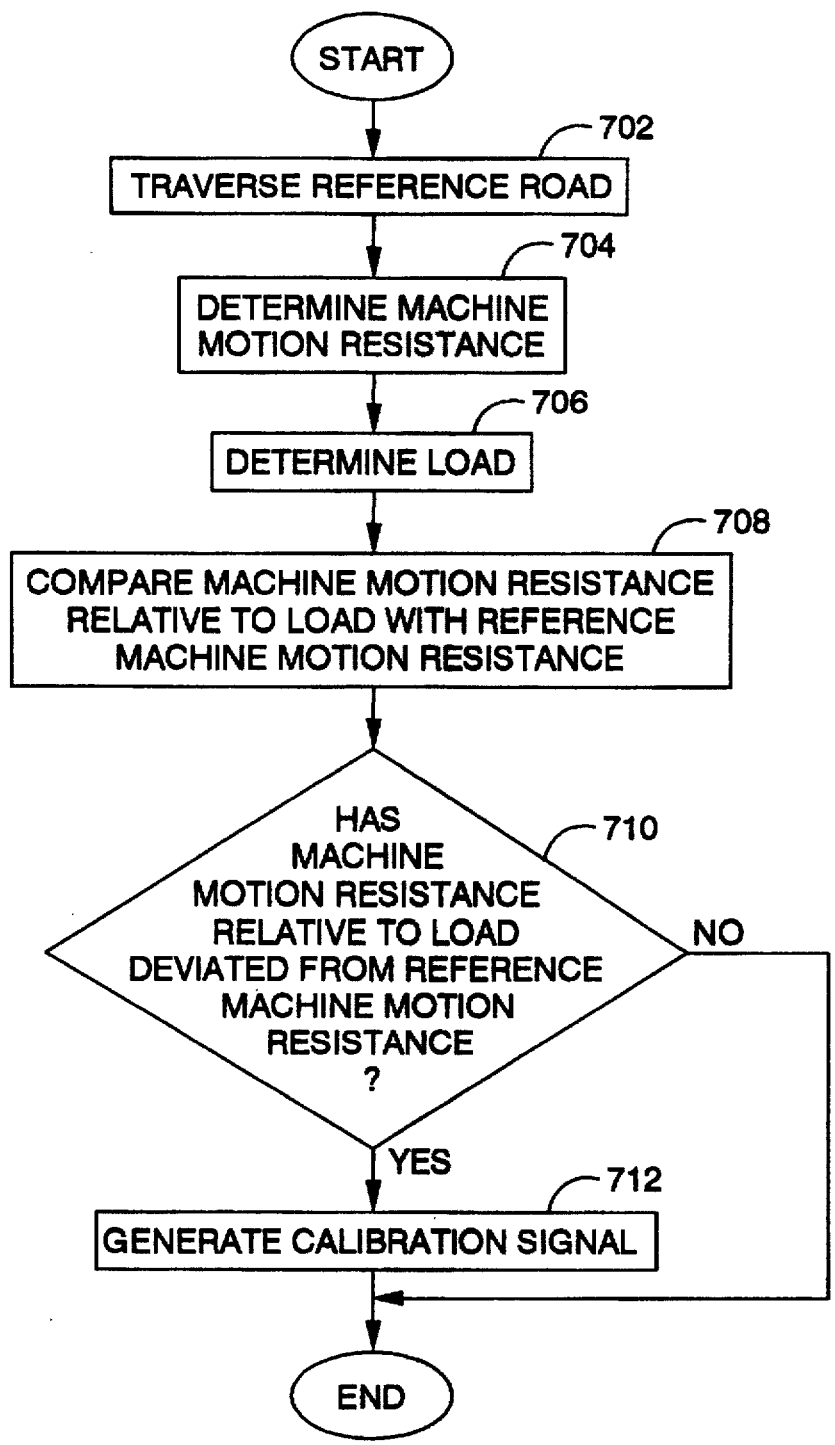
Fig_7

APPARATUS AND METHOD FOR DETERMINING A CONDITION OF A ROAD

TECHNICAL FIELD

This invention relates generally to an apparatus and method for determining a condition of a road and more particularly to an apparatus and method for monitoring a set of parameters of a load hauling machine and responsively determining a condition of a road.

BACKGROUND ART

Fleets of load hauling machines such as dump trucks are frequently used to haul materials throughout a work site. For example, in a large open mining site, dump trucks are used to haul ore and other mining materials from one location to another. At these sites, haul roads are created and maintained for the trucks to travel on.

As another example, trucks are used to haul logs at a logging site, using haul roads built and maintained throughout remote forests.

In these examples and others, fleets of load hauling machines are required to travel on haul roads that are located in harsh and constantly changing environments. The haul roads require constant monitoring and frequent maintenance to keep them suitable for the trucks to travel on. Deterioration of the haul roads creates conditions which can cause severe and costly damage to the load hauling machines, and can impede or even stop traffic on the road.

Several methods in the prior art attempt to monitor the condition of haul roads. For example, in U.S. Pat. No. 4,839,835, Hagenbuch discloses a system which monitors and counts spikes in a payload monitoring system to determine the presence of a road condition known as road roughness. Road roughness occurs when a section of road begins to buckle, creating a washboard effect. Road roughness can damage the suspension and tires of a load hauling machine.

However, it is well known in the art that road roughness is commonly caused by a condition known as road softness. A soft road tends to buckle as trucks travel over it. Hagenbuch's system only counts spikes to determine the already existing presence of road roughness and does not monitor conditions of a road which can lead to roughness. Monitoring conditions of the road that could lead to road roughness would allow road maintenance crews to prevent development of a situation that can cause costly damage to the load hauling machines.

It is known in the art that the motion resistance of a truck can be correlated to the hardness or softness of a road. For example, in U.S. patent application Ser. No. 08/616869 filed by Schricker on Mar. 15, 1996, a method is disclosed for detecting an abnormal condition of a road surface by monitoring motion resistance of a truck as it travels over the road and correlating the motion resistance of the truck to the condition of the road.

If a section of road is determined to be too soft, maintenance can be performed on the road to correct the condition before further deterioration of the road can occur, and thus prevent serious damage from happening to the trucks.

However, a determination of road softness may be due, at least in part, to the condition of the tires on the truck, which is a factor in machine motion resistance. Thus, simply monitoring machine motion resistance gives no indication if a problem is related to a condition of the road or a condition of a tire.

The present invention is directed to overcoming one or more of the problems as set forth above.

DISCLOSURE OF THE INVENTION

In one aspect of the present invention an apparatus for determining a condition of a road traversed by at least one load hauling machine is disclosed. The apparatus includes at least one parameter sensor adapted to sense a parameter of the load hauling machine and responsively deliver a parameter signal. The apparatus also includes a control system to monitor tire condition and generate a calibration signal.

In another aspect of the present invention a method for determining a condition of a road traversed by at least one load hauling machine is disclosed. The method includes the steps of sensing at least one parameter, determining a machine motion resistance, monitoring tire condition, and generating a calibration signal.

In still another aspect of the present invention a method for determining a condition of a road traversed by at least one load hauling machine having a plurality of tires is disclosed. The method includes the steps of traversing a reference section of the road, determining a machine motion resistance, determining a load on the tires, comparing the machine motion resistance relative to the load to a reference machine motion resistance, and generating a calibration signal.

BRIEF DESCRIPTION OF THE DRAWINGS

FIG. 1 is a diagrammatic illustration of a load hauling machine;

FIG. 2 is a block diagram illustrating an embodiment of the present invention;

FIG. 3 is a block diagram further illustrating the embodiment of FIG. 2;

FIG. 4 is a flow diagram illustrating a method for determining a condition of a road, according to an embodiment of the present invention;

FIG. 5 is a flow diagram illustrating a method for determining a machine motion resistance, according to the embodiment illustrated in FIG. 4;

FIG. 6 is a flow diagram illustrating a method for determining a slope resistance, according to the embodiment illustrated in FIG. 4; and FIG. 7 is a flow diagram illustrating a method for generating a calibration signal, according to another embodiment of the present invention.

BEST MODE FOR CARRYING OUT THE INVENTION

With reference to the drawings, and in particular to FIG. 1, an apparatus 100 for determining a condition of a road 104 traversed by at least one load hauling machine 102 is disclosed. The load hauling machine 102 has a plurality of tires 106 in contact with the road 104.

The load hauling machine 102 shown in FIG. 1 is an off-road mining truck capable of hauling large payloads of mining materials. However, the present invention may also apply to other types of load hauling machines, such as logging trucks, scrapers, and dump trucks.

The road 104 is typically a haul road built and maintained for the purpose of hauling loads throughout a work site or remote area. Maintenance and repair of the road 104 is normally the responsibility of the owner or operator of the site.

Referring to FIG. 2, at least one parameter sensor 202 is connected to the load hauling machine 102. The at least one parameter sensor 202 is adapted to sense a parameter of the load hauling machine 102 and deliver a responsive parameter signal to a control system 204 connected to the load hauling machine 102.

The control system 204 is adapted to monitor a condition of the tires 106 and generate a calibration signal. The control system 204 determines a condition of the road 104 in response to the parameter signal and the calibration signal.

Referring to FIG. 3, a more detailed diagram of the system of FIG. 2 is shown. A power sensor 302 is adapted to sense a power delivered by the load hauling machine 102 and deliver the parameter signal as a power signal.

A position sensor 304 is adapted to sense a position of the load hauling machine 102 and deliver a position signal to the control system 204. The control system 204 is adapted to determine a machine motion resistance in response to the power signal and the position signal.

It is known in the art that machine motion resistance can be determined by subtracting slope resistance (the resistance caused by a slope of the grade of the road 104), power train losses, and transient power loss (due to acceleration) from the total power generated by the load hauling machine 102. In one embodiment of the present invention, machine motion resistance is determined by signals received from the power sensor 302 and the position sensor 304. Other embodiments use other combinations of sensors as discussed below.

A slope sensor 306 connected to the load hauling machine 102 is adapted to sense the slope of the grade of the road 104 and deliver a parameter signal as a slope signal to the control system 204. One example of a slope sensor 306 is an inclinometer.

As another example of a slope sensor 306, the control system 204 is adapted to determine the slope of the grade of the road 104 by receiving changes in elevation from the position sensor 304 as the load hauling machine 102 traverses the road 104.

An acceleration sensor 308 connected to the load hauling machine 102 is adapted to sense acceleration of the load hauling machine 102 and deliver the parameter signal as an acceleration signal to the control system 204. One example of an acceleration sensor 308 is an accelerometer.

As another example of an acceleration sensor 308, the control system 204 is adapted to receive the position signal from the position sensor 304 and determine acceleration as a change in the rate of change of position of the load hauling machine 102 as the load hauling machine 102 traverses the road 104.

In one embodiment of the present invention, the position sensor 304 is a global positioning satellite (GPS) system. In another embodiment of the present invention, the position sensor 304 is a local reference positioning system, such as a laser positioning system. Other types of positioning systems, either global, local, or combinations of global and local, may be used without deviating from the present invention.

In one aspect of the present invention the control system 204 is adapted to monitor the condition of the tires 106 and generate a responsive calibration signal. It is known in the art that the machine motion resistance is affected by the condition of the tires 106. For example, tires that are soft, e.g., have low inflation, are known to increase machine motion resistance.

It is also known in the art that a condition of the road 104 known as road softness also affects machine motion resistance. For example, a road 104 that is soft will increase machine motion resistance. A road 104 that is soft will also deteriorate quickly and develop bumps and potholes, which can cause damage to the load hauling machines 102.

One aspect of the present invention is to determine sections of the road 104 that are soft. The control system 204 generates the calibration signal to compensate for softness in the tires 106, so a more accurate indication of softness of the road 104 can be determined.

In FIG. 3, a tire condition sensor 310 is adapted to deliver a tire condition signal to the control system 204, which calculates a responsive calibration signal. The tire condition sensor 310 may include inflation sensors suitable for monitoring tire condition directly, e.g., tire softness. The tire condition sensor 310 may also include other types of sensors. For example, the temperature of the tires 106 may be sensed and, if truck loading, truck speed, and time of truck motion are factored in, the softness of the tires 106 may be determined as being in proportion to excess heat generated by the tires 106.

A load sensor 312 is connected to the load hauling machine 102 and is adapted to deliver a load signal to the control system 204.

In the embodiment of the present invention discussed above, a calibration signal is generated in response to the condition of the tires 106.

In another embodiment of the present invention, the control system 204 is adapted to determine the machine motion resistance and receive the load signal and generate a responsive calibration signal as the load hauling machine 102 traverses a reference section of the road 108 that is in a known and controlled condition. The machine motion resistance of the reference section of the road 108 is known for a particular condition of the tires 106. As the load hauling machine 102 traverses the reference section of the road 108, the control system 204 compensates for changes in the load on the tires 106. Thus, any difference in the machine motion resistance from the previously known machine motion resistance corresponds to changes in the condition of the tires 106. The control system 204 determines any changes in the condition of the tires 106 and generates a responsive calibration signal.

Referring to FIGS. 4-6, a method for determining a condition of a road 104 traversed by at least one load hauling machine 102 having a plurality of tires 106 is shown.

In FIG. 4, in a first control block 402 a parameter of the load hauling machine 102 is sensed by at least one parameter sensor 202. In a second control block 404, a parameter signal responsive to the at least one parameter sensor 202 is delivered to the control system 204.

In a third control block 406, the control system 204 determines a machine motion resistance in response to the parameter signal.

The condition of the tires 106 is monitored in a fourth control block 408, and the control system 204 generates a calibration signal in response to the condition of the tires 106 in a fifth control block 410.

The calibration signal is calculated by the control system 204 to compensate for the machine motion resistance of the tires 106. If the tire size and type, the load on the tires 106, and the inflation pressure of the tires 106 is known, the machine motion resistance of the tires 106 can be determined in a number of ways. For example, tire manufacturers often provide lookup tables for tire motion resistance based on load and inflation pressure. As another example, tire motion resistance factors can be determined experimentally for various combinations of load and inflation pressures. Other methods of generating the calibration signal based on the machine motion resistance of the tires 106 can be used without deviating from the idea of the invention.

In a sixth control block 412, the control system 204 determines a condition of the road 104 in response to the machine motion resistance and the calibration signal. In a seventh control block 414, the position of the load hauling machine 102 is determined on the road 104 where the condition is determined.

In FIG. 5, a method for determining the machine motion resistance is shown.

In a first control block 502, a slope of the grade of the road 104 is sensed. The slope may be sensed directly with a slope sensor 306 such as an inclinometer or the slope may be determined by finding the difference in altitude of the load hauling machine 102 as it traverses the road 104 as sensed by the position sensor 304.

In a second control block 504, a slope resistance of the road 104 is determined. One method of determining the slope resistance is to take the sine of the angle that the slope of the road 104 makes with a horizontal reference plane. However, other methods of determining slope resistance, e.g., lookup tables, rise over run, etc., may be used.

In a third control block 506, a power delivered by the load hauling machine 102 is sensed and the total power consumed by the load hauling machine 102 is determined in a fourth control block 508.

In one embodiment of the present invention, power sensors 302 are used to sense the power generated by the load hauling machine 102. Power sensors 302 also sense power delivered to the tires 106. The power delivered to the tires 106 is defined as the total power consumed by the load hauling machine 102. The drivetrain power loss, which is defined as the difference between the power generated by the load hauling machine 102 and the power delivered to the tires 106 is determined in a fifth control block 510.

The transient power consumption due to acceleration of the load hauling machine 102, both positive and negative; is determined in a sixth control block 512. In one embodiment of the present invention, an acceleration sensor 308, such as an accelerometer, is used to sense acceleration of the load hauling machine 102. In another embodiment, acceleration is determined by sensing positions of the load hauling machine 102 by the position sensor 304 as the load hauling machine 102 traverses the road 104 and determining any change in the rate of change of position.

The transient power consumption is determined by determining the difference in power consumed by the load hauling machine 102 as it accelerates or decelerates as compared to the power consumed by the load hauling machine 102 when acceleration is zero. The transient power consumption may be measured directly by the power sensors 302 discussed above or determined indirectly by correlating acceleration to power consumption with the load on the tires 106 factored in. As an alternative embodiment, the machine motion resistance may be determined only when the acceleration sensor 308 senses that acceleration is zero, thereby eliminating transient power consumption as a factor.

Machine motion resistance can be determined as slope resistance, power train losses, and transient power loss subtracted from total machine power. In the embodiment of the invention discussed above, the power components needed to determine machine motion resistance are determined at various points on the load hauling machine 102. However, in an alternative embodiment, power may be determined by comparing the power consumed by the load hauling machine 102 on a reference section of the road 108, the reference section of the road 108 being in a known and controlled condition, to the power consumed by the load hauling machine 102 as it traverses the haul road 104. The difference in power consumption between the reference section of the road 108 and the haul road 104 correlates to the softness of the road 104, which is one of the road conditions desired to determine.

Still referring to FIG. 5, in a seventh control block 514 the machine motion resistance is calculated as a function of the slope resistance, the total power consumed, the drivetrain power loss, and the transient power consumption.

Referring to FIG. 6, a method for determining the slope resistance is disclosed. In a first control block 602, a first value of elevation is sensed by the position sensor 304 at a first position of the load hauling machine 102 on the road 104. In a second control block 604, a second value of elevation is sensed by the position sensor 304 at a second position of the load hauling machine 102 on the road 104.

In a third control block 606, the difference between the first value of elevation and the second value of elevation is calculated and the slope of the grade of the road 104 is calculated from the first position to the second position. The slope resistance is then determined from the slope of the grade of the road 104 in a fourth control block 608.

Referring to FIG. 7, an alternative method for determining a condition of a road 104 traversed by at least one load hauling machine 102 having a plurality of tires 106 in contact with the road 104 is disclosed.

In a first control block 702, the load hauling machine 102 traverses a reference section of the road 108, the reference section of the road 108 being in a known and controlled condition. For example, the reference section of the road 108 may be a section of the haul road 104 that is maintained at a constant and known hardness. The reference section of the road 108 may also be located at a site that is relatively horizontal and flat, thus eliminating slope resistance from machine motion resistance. The reference section of the road 108 may also be located in the site where the load hauling machines 102 traverse it on a regular basis.

In a second control block 704, at least one parameter of the load hauling machine 102 is sensed and a responsive parameter signal is delivered to the control system 204. The control system 204 responsively determines the machine motion resistance.

A load on the tires 106 is determined in a third control block 706. The load may be determined by any of a number of methods known in the art. For example, monitoring a load hauling machine's suspension, monitoring frame stresses, and monitoring axle and wheel loads are a few methods that can be used.

In a fourth control block 708, the machine motion resistance relative to the load is compared to a reference machine motion resistance. The machine motion resistance relative to the load accounts for variations in the load each time the load hauling machine 102 traverses the reference section of the road 108. The variations in the load are known in the art to be in a direct linear relationship to the machine motion resistance. Therefore the machine motion resistance relative to the load should remain constant if the condition of the road 104 is constant and the condition of the tires 106 does not change.

The reference machine motion resistance may be a machine motion resistance factor determined experimentally or it may be the machine motion resistance determined during a previous pass over the reference section of the road 108 by the load hauling machine 102. Other methods for determining a reference machine motion resistance may be used without deviating from the purpose of the invention.

In a first decision block 710, the deviation of the machine motion resistance relative to the load from the reference machine motion resistance is analyzed. If there is no deviation then the condition of the tires 106 is assumed not to have changed and control proceeds to the end of the flowchart. If there is deviation then control proceeds to a fifth control block 712 where the control system 204 generates a calibration signal to compensate for changes in the condition of the tires 106. The calibration signal is the numeric value of the change in machine motion resistance to the reference machine motion resistance. The value of the calibration signal is then subtracted from the machine motion resistance determined on the haul road 104 to eliminate all variables except for changes in machine motion resistance caused by the softness of the road 104.

Industrial Applicability

As an example of one embodiment of the present invention, a fleet of load hauling machines 102, e.g., off-road mining trucks, haul material on haul roads 104 at a mining site. As the load hauling machines 102 traverse the haul roads 104, at least one parameter sensor 202 on board each load hauling machine 102 senses a parameter and delivers a responsive parameter signal to a control system 204. The control system 204 determines a machine motion resistance in response to the parameter signal.

A tire condition sensor 310 monitors the condition of the tires 106 and delivers a tire condition signal to the control system 204, which responsively generates a calibration signal. The control system determines a condition of the road 104 in response to the machine motion resistance and the calibration signal.

Specifically, in the example above, the calibration signal compensates for softness of the tires 106. The determined condition of the road 104 is then determined to be road softness. A position sensor 304 determines the position of the load hauling machine 102 on the road 104 where the road softness is determined. Maintenance can then be performed on the section of the road 104 determined to be soft to prevent deterioration of the road 104.

As an example of another embodiment of the present invention, a fleet of load hauling machines 102, e.g., off-road mining trucks, haul material on haul roads 104 at a mining site. A reference section of the haul road 108 is maintained in a known and controlled condition. For example, the reference section of the road 108 has a known and controlled hardness and is located so that the slope of the grade is zero or negligible.

As a load hauling machine 102 traverses the haul road 104 it repeatedly passes over the reference section of the road 108. When the load hauling machine 102 traverses the reference section of the road 108, the machine motion resistance is determined by the same methods as the example described prior to this example.

A load sensor 312 senses a load on the tires 106 and delivers a load signal to the control system 204. The control system 204 determines the machine motion resistance relative to the load to compensate for varying loads for each pass over the reference section of the road 108. The motion resistance relative to the load is compared to a reference machine motion resistance.

The reference machine motion resistance may be determined experimentally or may be the determined machine motion resistance from a previous pass by the load hauling machine 102 over the reference section of the road 108.

If the machine motion resistance relative to the load has deviated from the reference machine motion resistance, the condition of the tires 106, e.g., softness, is determined to have changed and the control system 204 generates a calibration signal and the road condition for the haul road 104 is determined in the same manner as the previous example.

Other aspects, objects, and features of the present invention can be obtained from a study of the drawings, the disclosure, and the appended claims.

I claim:

1. An apparatus for determining a condition of a road traversed by at least one load hauling machine having a plurality of tires in contact with said road, comprising:

at least one parameter sensor connected to said load hauling machine, said at least one parameter sensor being adapted to sense a parameter of said load hauling machine and responsively deliver a parameter signal; and a control system connected to said load hauling machine, said control system being adapted to monitor a condition of said tires and responsively generate a calibration signal, and to receive said parameter signal and determine a condition of said road in response to said parameter signal and said calibration signal.

2. An apparatus, as set forth in claim 1, wherein said at least one parameter sensor is a power sensor adapted to sense a power delivered by said load hauling machine and wherein said parameter signal is a power signal;

said apparatus further includes a position sensor adapted to sense a position of said load hauling machine and deliver a responsive position signal; and wherein said control system is adapted to receive said power signal and said position signal and responsively determine a machine motion resistance.

3. An apparatus, as set forth in claim 2, wherein said at least one parameter sensor includes a slope sensor adapted to sense a slope of the grade of said road and wherein said machine motion resistance is a function of said slope.

4. An apparatus, as set forth in claim 3, wherein said slope sensor includes an inclinometer.

5. An apparatus, as set forth in claim 2, wherein said control system is adapted to receive said position signal and responsively determine a slope of the grade of said road and wherein said machine motion resistance is a function of said slope.

6. An apparatus, as set forth in claim 2, wherein said at least one parameter sensor includes an acceleration sensor adapted to sense an acceleration of said load hauling machine and wherein said machine motion resistance is a function of said acceleration.

7. An apparatus, as set forth in claim 6, wherein said acceleration sensor includes an accelerometer.

8. An apparatus, as set forth in claim 2, wherein said control system is adapted to receive said position signal and responsively determine an acceleration of said load hauling machine and wherein said machine motion resistance is a function of said acceleration.

9. An apparatus, as set forth in claim 2, wherein said position sensor includes a global positioning satellite (GPS) system.

10. An apparatus, as set forth in claim 2, wherein said position sensor includes a local reference positioning system.

11. An apparatus, as set forth in claim 10, wherein said local reference positioning system includes a laser positioning system.

12. An apparatus, as set forth in claim 2, including a tire condition sensor adapted to deliver a tire condition signal.

13. An apparatus, as set forth in claim 12, wherein said control system is adapted to receive said tire condition signal and responsively calculate said calibration signal.

14. An apparatus, as set forth in claim 2, including a load sensor adapted to deliver a load signal.

15. An apparatus, as set forth in claim 14, wherein said control system is adapted to receive said machine motion resistance signal and said load signal and responsively generate said calibration signal as said load hauling machine traverses a reference section of said road, said reference section being in a known and controlled condition.

16. A method for determining a condition of a road traversed by at least one load hauling machine having a plurality of tires in contact with said road, including the steps of:
sensing at least one parameter of said load hauling machine and responsively delivering a parameter signal;
determining a machine motion resistance in response to said parameter signal;
monitoring a condition of said tires and responsively generating a calibration signal; and
receiving said calibration signal and determining a condition of said road in response to said machine motion resistance and said calibration signal.

17. A method, as set forth in claim 16, further including the step of determining the position of said load hauling machine where said condition is determined.

18. A method, as set forth in claim 17, including the steps of:
sensing a slope of the grade of said road and responsively determining a slope resistance of said road as a function of said parameter signal;
sensing a power delivered by said load hauling machine and responsively determining a total power consumed by said load hauling machine as a function of said parameter signal;
determining a drivetrain power loss of said load hauling machine and a transient power consumption of said load hauling machine as functions of said parameter signal; and
receiving said slope resistance, said total power consumed, said drivetrain power loss, and said transient power consumption and responsively calculating said machine motion resistance.

19. A method, as set forth in claim 18, wherein the step of determining said slope resistance includes the steps of:

sensing a first value of elevation at a first position of said load hauling machine on said road;
sensing a second value of elevation at a second position of said load hauling machine on said road;
determining said slope of the grade of said road from said first position to said second position in response to the difference between said first value of elevation and said second value of elevation; and
calculating said slope resistance from said first position to said second position in response to said slope.

20. A method for determining a condition of a road traversed by at least one load hauling machine having a plurality of tires in contact with said road, including the steps of:
traversing a reference section of said road, said reference section being in a known and controlled condition;
sensing at least one parameter of said load hauling machine and responsively delivering a parameter signal; determining a load on said tires;
determining a machine motion resistance relative to the load in response to said parameter signal;
comparing said machine motion resistance relative to said load to a reference machine motion resistance; and
generating a calibration signal in response to a difference between said machine motion resistance relative to said load and said reference machine motion resistance; and
determining a condition of said road in response to said calibration signal.

21. An apparatus for determining a condition of a road traversed by at least one load hauling machine having a plurality of tires in contact with said road, comprising:
a slope sensor adapted to sense a slope of the grade of said road and deliver a responsive slope signal;
a power sensor adapted to sense a power delivered by said load hauling machine and deliver a responsive power signal;
an acceleration sensor adapted to sense an acceleration of said load hauling machine and deliver a responsive acceleration signal;
a position sensor adapted to sense a position of said load hauling machine and deliver a responsive position signal; and
a control system connected to said load hauling machine, said control system being adapted to monitor a condition of said tires and responsively generate a calibration signal, and to receive said slope signal, said power signal, said acceleration signal, and said position signal and determine a condition of said road in response to said slope signal, said power signal, said acceleration signal, said position signal, and said calibration signal.

* * * * *